(12) United States Patent
Okamoto et al.

(10) Patent No.: US 8,357,828 B2
(45) Date of Patent: Jan. 22, 2013

(54) PROCESSES FOR PRODUCING 1,1-DICHLORO-2,3,3,3-TETRAFLUOROPROPENE AND 2,3,3,3-TETRAFLUOROPROPENE

(75) Inventors: Hidekazu Okamoto, Tokyo (JP); Yasuyuki Sasao, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/163,809

(22) Filed: Jun. 20, 2011

(65) Prior Publication Data

US 2011/0251442 A1    Oct. 13, 2011

Related U.S. Application Data

(63) Continuation of application No. PCT/JP2009/071649, filed on Dec. 25, 2009.

(30) Foreign Application Priority Data

Dec. 25, 2008 (JP) .................... 2008-331321

(51) Int. Cl.
*C07C 21/18* (2006.01)
(52) U.S. Cl. ........ 570/151; 570/135; 570/136; 570/156; 570/157
(58) Field of Classification Search .................. None
See application file for complete search history.

(56) References Cited

U.S. PATENT DOCUMENTS

| | | | | |
|---|---|---|---|---|
| 5,157,171 A | * | 10/1992 | Sievert et al. ............ | 570/151 |
| 6,548,719 B1 | * | 4/2003 | Nair et al. ............... | 570/157 |
| 2003/0060670 A1 | | 3/2003 | Nair et al. | |
| 2010/0022808 A1 | * | 1/2010 | Rao et al. ............... | 570/156 |
| 2010/0185028 A1 | | 7/2010 | Okamoto | |
| 2011/0172469 A1 | | 7/2011 | Okamoto | |

FOREIGN PATENT DOCUMENTS

| | | |
|---|---|---|
| JP | 8-169850 | 7/1996 |
| JP | 8-193039 | 7/1996 |
| JP | 3778298 | 3/2006 |
| WO | 2008/060612 | 5/2008 |
| WO | 2008/060614 | 5/2008 |

OTHER PUBLICATIONS

International Search Report issued Feb. 2, 2010 in PCT/JP09/071649 filed Dec. 25, 2009.
Extended European Search Report issued Jun. 28, 2012, in Patent Application No. 09835050.7.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

To provide a simple and economical process for producing 1,1-dichloro-2,3,3,3-tetrafluoropropene, which does not require purification of the raw material component obtained in the form of a mixture of isomers, and a process for producing 2,3,3,3-tetrafluoropropene from the product thereby obtained.

A process for producing 1,1-dichloro-2,3,3,3-tetrafluoropropene, characterized by bringing a mixture of dichloropentafluoropropane isomers which contains 1,1-dichloro-2,2,3,3,3-pentafluoropropane into contact with an aqueous alkali solution in the presence of a phase transfer catalyst, and thereby selectively dehydrofluorinating only the 1,1-dichloro-2,2,3,3,3-pentafluoropropane in the mixture, and a process for producing 2,3,3,3-tetrafluoropropene from the 1,1-dichloro-2,3,3,3-tetrafluoropropene thereby obtained.

18 Claims, No Drawings

PROCESSES FOR PRODUCING 1,1-DICHLORO-2,3,3,3-TETRAFLUOROPROPENE AND 2,3,3,3-TETRAFLUOROPROPENE

TECHNICAL FIELD

The present invention relates to processes for producing 1,1-dichloro-2,3,3,3-tetrafluoropropene and 2,3,3,3-tetrafluoropropene.

BACKGROUND ART 1,1-Dichloro-2,3,3,3-tetrafluoropropene (CFO-1214ya) is a compound useful as a synthetic raw material for 2,3,3,3-tetrafluoropropene (HFO-1234yf) which is expected in recent years as a new refrigerant to be substituted for 1,1,1,2-tetrafluoroethane (HFC-134a) being a greenhouse gas. In this specification, with respect to a halogenated hydrocarbon, the compound name may be followed by an abbreviated name of the compound in parenthesis, but in this specification the abbreviated name may be employed instead of the compound name, as the case requires.

As a method for producing such 1,1-dichloro-2,3,3,3-tetrafluoropropene (CFO-1214ya), a method has been known wherein, as a raw material, 1,1-dichloro-2,2,3,3,3-pentafluoropropane (HCFC-225ca) is dehydrofluorinated by an aqueous alkali solution in the presence of a phase transfer catalyst or by a gas phase reaction in the presence of a catalyst such as chromium, iron, copper or activated carbon (Patent Document 1).

Here, 1,1-dichloro-2,2,3,3,3-pentafluoropropane (HCFC-225ca) to be used as a raw material in the above method is usually produced in the form of a mixture with 1,3-dichloro-1,2,2,3,3-pentafluoropropane (HCFC-225cb), 2,2-dichloro-1,1,3,3,3-pentafluoropropane (HCFC-225aa) and/or other dichloropentafluoropropane isomers (Patent Document 2, Non-Patent Document 1), and therefore, one separated and purified from such a mixture of isomers has been employed as a raw material in the above production method.

However, with respect to the above dichloropentafluoropropane isomers, their boiling points are rather close to one another, whereby their separation and purification are difficult by a usual separation/purification technique (such as distillation), and in order to produce highly pure 1,1-dichloro-2,2,3,3,3-pentafluoropropane (HCFC-225ca) on an industrial scale, a multi-stage distillation, etc. are required.

When the production is comprehensively considered including the preparation of the raw material, etc., the above-mentioned conventional method for producing 1,1-dichloro-2,3,3,3-tetrafluoropropene (CFO-1214ya) can hardly be regarded as a simple and economical production method.

PRIOR ART DOCUMENTS

Patent Documents
  Patent Document 1: Japanese Patent No. 3,778,298
  Patent Document 2: U.S. Pat. No. 5,157,171
Non-Patent Document
  Non-Patent Document 1: "Fluorine Chemistry Reviews, Vol. 8", p. 39-71, compiled by Paul Tarrant, published by MARCEL DEKKER, INC. in 1967

DISCLOSURE OF INVENTION

Technical Problem

The present invention has been made from the above-mentioned viewpoint and is to provide a simple and economical process for producing 1,1-dichloro-2,3,3,3-tetrafluoropropene (CFO-1214ya), which does not require purification of the raw material component i.e. 1,1-dichloro-2,2,3,3,3-pentafluoropropane (HCFC-225ca) obtained in the form of a mixture of isomers, and to provide a process for producing 2,3,3,3-tetrafluoropropene (HFO-1234yf) from the product thereby obtained.

Solution to Problem

The present invention has been made to solve the above problem and provides a process for producing 1,1-dichloro-2,3,3,3-tetrafluoropropene (CFO-1214ya), characterized by bringing a mixture of dichloropentafluoropropane (HCFC-225) isomers which contains 1,1-dichloro-2,2,3,3,3-pentafluoropropane (HCFC-225ca) into contact with an aqueous alkali solution in the presence of a phase transfer catalyst, and thereby selectively dehydrofluorinating only the 1,1-dichloro-2,2,3,3,3-pentafluoropropane (HCFC-225ca) in the mixture.

Further, the present invention provides a process for producing 2,3,3,3-tetrafluoropropene (HFO-1234yf), which comprises reacting the 1,1-dichloro-2,3,3,3-tetrafluoropropene (CFO-1214ya) obtained by the above process, with hydrogen in the presence of a catalyst.

Advantageous Effects of Invention

By the process of the present invention, is possible to simply and economically produce 1,1-dichloro-2,3,3,3-tetrafluoropropene (CFO-1214ya) without requiring purification of the raw material component i.e. 1,1-dichloro-2,2,3,3-pentafluoropropane (HCFC-225ca) obtained in the form of a mixture of isomers. Further, by using the 1,1-dichloro-2,3,3,3-tetrafluoropropene (CFO-1214ya) obtained by this process, it becomes possible to economically produce 2,3,3,3-tetrafluoropropene (HFO-1234yf).

DESCRIPTION OF EMBODIMENTS

Now, embodiments of the present invention will be described.

The process for producing 1,1-dichloro-2,3,3,3-tetrafluoropropene (CFO-1214ya) of the present invention is characterized in that a mixture of dichloropentafluoropropane (HCFC-225) isomers which contains 1,1-dichloro-2,2,3,3,3-pentafluoropropane (HCFC-225ca) is used as a raw material component, and this mixture is brought in contact with an aqueous alkali solution in the presence of a phase transfer catalyst thereby to selectively dehydrofluorinate only the 1,1-dichloro-2,2,3,3,3-pentafluoropropane (HCFC-225ca) in the mixture.

Firstly, the mixture of dichloropentafluoropropane ($C_3HCl_2F_5$, HCFC-225) isomers which contains 1,1-dichloro-2,2,3,3,3-pentafluoropropane ($CHCl_2CF_2CF_3$, HCFC-225ca) to be used as the raw material component, will be described.

The mixture of the HCFC-225 isomers to be used in the present invention is a mixture of HCFC-225 isomers which contains HCFC-225ca, and in other words, it is a mixture of HCFC-225 isomers, which contains HCFC-225ca and at least one HCFC-225 isomer other than HCFC-225ca.

HCFC-225 isomers contained in the mixture of isomers in addition to the HCFC-225ca are not particularly limited, but specifically, they may, for example, be 1,3-dichloro-1,2,2,3,3-pentafluoropropane ($CHClFCF_2CClF_2$, HCFC-225cb), 2,2-dichloro-1,1,3,3,3-pentafluoropropane ($CHF_2CCl_2CF_3$, HCFC-225aa), 1,2-dichloro-1,2,3,3,3-pentafluoropropane ($CHClFCClFCF_3$, HCFC-225ba) and 2,3-dichloro-1,1,2,3,3-pentafluoropropane ($CHF_2CClFCClF_2$, HCFC-225bb). The mixture of HCFC-225 isomers to be used in the present invention is constituted by one or more of them, and HCFC-225ca.

The content of HCFC-225ca in the mixture of HCFC-225 isomers to be used in the present invention is not particularly limited, but from the viewpoint of the reactor efficiency, it is preferably at least 10 mol %. On the other hand, from the efficiency for separating and purifying HCFC-225ca from an industrial product of HCFC-225 obtained in the form of a mixture of isomers, the content of HCFC-225ca in the mixture of HCFC-225 isomers is preferably at most 99.5 mol %.

Further, in the process for producing CFO-1214ya of the present invention, as such a mixture of HCFC-225 isomers which contains HCFC-225ca, it is possible to employ a mixture of HCFC-225 isomers, which is obtainable as follows.

Firstly, dichloropentafluoropropane (HCFC-225) is usually produced by reacting tetrafluoroethylene and dichlorofluoromethane in the presence of a catalyst, as shown by the following reaction formula (1), but HCFC-225 obtainable by this reaction is not formed as a compound having a single structure, but is formed in the form of a mixture of at least two isomers.

[Reaction to Form HCFC-22.5 (Mixture of Isomers)]

$$CF_2=CF_2+CHCl_2F \rightarrow C_3HCl_2F_5 (HCFC\text{-}225) \quad (1)$$

With respect to the mixture of isomers of dichloropentafluoropropane ($C_3HCl_2F_5$, HCFC-225) obtainable by the reaction represented by the above formula (1), the types and proportions of the isomers constituting the mixture vary depending upon the reaction conditions, particularly the type of the catalyst to be used, but in most cases, such a mixture of HCFC-225 isomers is one containing HCFC-225ca and thus is a mixture of isomers, which is useful for the process of the present invention.

More specifically, for example, in a reaction employing aluminum chloride as the catalyst which is commonly widely carried out among reactions represented by the above reaction formula (1), the obtainable mixture of HCFC-225 isomers is one which contains mainly HCFC-225ca and HCFC-225cb as the reaction products, or a mixture of isomers which further contains a small amount of HCFC-225aa, HCFC-225bb, etc., and it is useful as the raw material component for the present invention.

Further, it is possible to employ, as the raw material component of the present invention, a mixture of HCFC-225 isomers, which contains mainly HCFC-225ca, HCFC-225cb and HCFC-225aa, and, as small amount components, HCFC-225bb, HCFC-225ba, etc. as reaction products, obtained by carrying out the reaction of the above reaction formula (1) by using a modified aluminum chloride treated with e.g. trichlorofluoromethane as the catalyst (U.S. Pat. No. 5,157,171).

Still further, it is also possible to employ, as the raw material component of the present invention, a mixture of HCFC-225 isomers, which contains mainly HCFC-225ca and HCFC-225cb, and, as small amount components, HCFC-225aa, HCFC-225bb, etc. as reaction products, obtained by carrying out the reaction of the above reaction formula (1) by using, as the catalyst, a Lewis acid catalyst, for example, a halogenated product containing at least one element selected from the group consisting of Al, Sb, Nb, Ta, W, Re, B, Sn, Ga, In, Zr, Hf and Ti (JP-B-7-98761).

As the mixture of HCFC-225 isomers to be used as the raw material component in the process for producing CFO-1214ya of the present invention, it is also possible to employ a mixture of HCFC-225 isomers which is obtainable by a reaction route other than one represented by the above reaction formula (1), so long as it is a mixture of isomers containing HCFC-225ca.

For example, it is possible to employ one obtained by isomerizing one of HCFC-225 isomers or a mixture of two or more HCFC-225 isomers by a catalytic reaction to a mixture of HCFC-225 isomers of another type or composition (U.S. Pat. No. 5,157,171), so long as such a mixture of isomers contains HCFC-225ca.

As described above, a mixture of HCFC-225 isomers containing HCFC-225ca to be used as the raw material component in the process of the present invention, is formed, but in the process of the present invention, it is preferred to employ a reaction composition obtained in each of the above described methods by separating and purifying it into a mixture of HCFC-225 isomers which contains HCFC-225ca.

Dichloropentafluoropropane (HCFC-225) is commonly widely used in the form of a mixture of HCFC-225 isomers, in a case where it is used in a field or application where no separation or purification is required as a specific isomer, for example, in an application as a cleaning agent, a diluting solvent, etc., and thus is available also as a commercial product. Therefore, it is also possible to use such a commercial product in the present invention.

One commercially available as a mixture of dichloropentafluoropropane (HCFC-225) isomers may, for example, be ASAHIKLIN AK-225 (tradename, manufactured by Asahi Glass Company, Limited, containing 48 mol % of HCFC-225ca and 52 mol % of HCFC-225cb).

Here, in the process for producing CFO-1214ya of the present invention, it is also possible to carry out the following dehydrofluorination reaction by using a reaction raw material composition containing the mixture of HCFC-225 isomers and other organic compounds, as the case requires and within a range not to impair the effects of the present invention. The organic compounds which may be contained in addition to the mixture of HCFC-225 isomers in the reaction raw material composition may, specifically be chloroform, chlorodifluoromethane, trifluoromethane, 1,1,3-trichloro-2,2,3,3-tetrafluoropropane, etc., and their content is preferably less than 10 mass % based on the total amount of the reaction raw material composition.

The process for producing 1,1-dichloro-2,3,3,3-tetrafluoropropene ($CF_3CF=CCl_2$, CFO-1214ya) of the present invention is characterized by using the above described mixture of HCFC-225 isomers which contains HCFC-225ca, as the raw material component, and bringing it in contact with an aqueous alkali solution in the presence of a phase transfer catalyst and thereby selectively dehydrofluorinating only 1,1-dichloro-2,2,3,3,3-pentafluoropropane (HCFC-225ca) in the mixture, as shown by the following reaction formula (2).

[Reaction for forming CFO-1214ya]

$$CF_3CF_2CHCl_2(HCFC\text{-}225ca)+n HCFC\text{-}225X \rightarrow CF_3CF=CCl_2(CFO\text{-}1214ya)+HF+n HCFC\text{-}225X \quad (2)$$

(in the reaction formula (2), HCFC-225X represents one or more of HCFC-225 isomers other than HCFC-225ca, n represents the molar amount of HCFC-225X per 1 mol of HCFC-225ca in the raw material mixture of HCFC-225 isomers and is a number larger than 0, and in the above formula, n is preferably from 0.005 to 9.)

Here, only HCFC-225ca is selectively dehydrofluorinated, and in the reaction represented by the above reaction formula (2), a reaction wherein HCFC-225X undergoes a dehydrofluorination reaction to form an isomer ($C_3Cl_2F_4$) of CFO-1214ya, may be included, if it is very little as compared with the quantity of the reaction wherein HCFC-225ca is dehydrofluorinated. In this specification, description will be made on such a basis that the reaction of the reaction formula (2)

contains a reaction wherein such a very little amount of HCFC-225X is dehydrofluorinated. Here, the "very little amount" may, for example, be a case wherein per 1 mol of HCFC-225X in the raw material mixture of HCFC-225 isomers, the quantity of the dehydrofluorination reaction is substantially less than 0.01 mol, and such a reaction quantity is preferably 0 mol, but may, in reality, be determined by the proportion of HCFC-225X contained in the mixture of isomers.

The aqueous alkali solution to be used for the dehydrofluorination reaction represented by the above reaction formula (2) is not particularly limited so long as it is an aqueous solution of a basic compound capable of carrying out the above dehydrofluorination reaction. Specifically, the reaction can be carried out by an aqueous solution of an inorganic basic compound, such as an alkali metal hydroxide such as potassium hydroxide or sodium hydroxide, or an alkaline earth metal hydroxide such as calcium hydroxide, an organic basic compound such as an amine, or an alkali metal alkoxide. However, from the viewpoint of the economical efficiency, it is preferred to employ an aqueous solution of an inorganic basic compound, and from the viewpoint of the reaction activity or selectivity, it is more preferred to employ an aqueous solution of sodium hydroxide or potassium hydroxide.

The concentration of the aqueous alkali solution to be used for the dehydrofluorination reaction is not particularly limited. However, in the present invention, it is preferably from 0.5 mass % to 40 mass %, as the mass % of the solute to the solution, from such a viewpoint that HCFC-225ca in the raw material mixture of HCFC-225 isomers will more selectively be dehydrofluorinated, and the concentration is more preferably from 5 mass % to 40 mass %. If the concentration of the aqueous alkali solution is less than 0.5 mass %, no adequate container efficiency of the reactor may sometime be obtainable, and if it exceeds 40 mass %, a dehydrohalogenation reaction of isomers other than HCFC-225ca may sometimes be promoted.

Further, the amount of the aqueous alkali solution to be used for the dehydrofluorination reaction represented by the above reaction formula (2) is not particularly limited so long as it is an amount whereby the above dehydrofluorination reaction can be carried out, but it is preferably adjusted so that it becomes an alkali amount of from 0.5 to 1.5 mol equivalent to the amount of HCFC-225ca to be used for the reaction, and more preferably, it is an alkali amount of from 1.0 to 1.3 mol equivalent.

In the dehydrofluorination reaction represented by the above formula (2), the mixture of HCFC-225 isomers to be subjected to the reaction and the aqueous alkali solution to act thereon have no compatibility. Therefore, in order to efficiently carry out the contact of the two, in the process of the present invention, the reaction is carried out by means of a phase transfer catalyst which is soluble in both water and the non-water soluble organic solvent.

As the phase transfer catalyst to be used for the dehydrofluorination reaction represented by the above reaction formula (2) in the present invention, a phase transfer catalyst which is commonly used may be mentioned without any particular restriction. Such a phase transfer catalyst may specifically be a quaternary ammonium salt, a quaternary phosphonium salt, a quaternary arsonium salt, a sulfonium salt, a crown ether or the like. As such a quaternary ammonium salt, a compound represented by the following formula (1) (hereinafter referred to as compound (i) as the case requires) may specifically be mentioned.

(in the formula (i), each of $R^{11}$ to $R^{14}$ which are independent of one another, is a hydrocarbon group, and $Y^-$ is an anion.)

In the above formula (i), each of $R^{11}$ to $R^{14}$ representing a hydrocarbon group is more specifically a group having the following characteristics.

Each of $R^{11}$ to $R^{14}$ may, for example, be an alkyl group, a cycloalkyl group, an alkenyl group, a cycloalkenyl group or an aryl group, and an alkyl group or an aryl group is preferred.

The number of carbon atoms in $R^{11}$ to $R^{14}$ is preferably from 4 to 100 as the total number of carbon atoms per one molecule of $R^{11}R^{12}R^{13}R^{14}N^+$.

$R^{11}$ to $R^{14}$ may, respectively, be the same groups or different groups.

Each of $R^{11}$ to $R^{14}$ may be substituted by a functional group which is inert under the reaction conditions. Such an inert functional group varies depending upon the reaction conditions, but may, for example, be a halogen atom, an ester group, a nitrile group, an acyl group, a carboxy group or an alkoxy group.

$R^{11}$ to $R^{14}$ may be linked to one another to form a hetero ring such as a nitrogen-containing hetero ring.

$R^{11}$ to $R^{14}$ may be a part of a polymer compound.

Specifically, the quaternary ammonium ion $R^{11}R^{12}R^{13}R^{14}N^+$ having such $R^{11}$ to $R^{14}$ may, for example, be a tetramethylammonium ion, a tetraethylammonium ion, a tetra-n-propylammonium ion, a tetra-n-butylammonium ion, a tri-n-octylmethylammonium ion, a cetyltrimethylammonium ion, a benzyltrimethylammonium ion, a benzyltriethylammonium ion, a cetylbenzyldimethylammonium ion, a cetylpyridinium ion, a n-dodecylpyridinium ion, a phenyltrimethylammonium ion, a phenyltriethylammonium ion, an N-benzylpicolinium ion, a pentamethonium ion or a hexamethonium ion.

Further, in the above formula (i), $Y^-$ representing an anion may specifically be e.g. a chlorine ion, a fluorine ion, a bromine ion, an iodine ion, a sulfate ion, a nitrate ion, a phosphate ion, a perchlorate ion, a hydrogen sulfate ion, a hydroxy-ion, an acetate ion, a benzoate ion, a benzene sulfonate ion or a p-toluene sulfonate ion, and a chlorine ion, a bromine ion, an iodine ion, a hydrogen sulfate ion or a hydroxy-ion is preferred.

Here, as the compound (i), a combination of the following $R^{11}R^{12}R^{13}R^{14}N^+$ and the following $Y^-$ is preferred from the viewpoint of the general versatility and reactivity of the compound (i).

$R^{11}R^{12}R^{13}R^{14}N^+$: a tetramethylammonium ion, a tetraethylammonium ion, a tetra-n-propylammonium ion, a tetra-n-butylammonium ion or a tri-n-octylmethylammonium ion.

$Y^-$: a fluorine ion, a chlorine ion or a bromine ion

The above quaternary phosphonium salt may specifically be a compound represented by the following formula (ii) (hereinafter referred to as compound (ii) as the case requires):

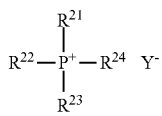

(in the formula (ii), each of $R^{21}$ to $R^{24}$ which are independent of one another, is a hydrocarbon group, and $Y^-$ is an anion.)

In the above formula (ii), each of $R^{21}$ to $R^{24}$ representing a hydrocarbon group is more specifically a group having the following characteristics.

Each of $R^{21}$ to $R^{24}$ may, for example, be an alkyl group, a cycloalkyl group, an alkenyl group, a cycloalkenyl group or an aryl group, and an alkyl group or an aryl group is preferred.

The number of carbon atoms in $R^{21}$ to $R^{24}$ is preferably from 4 to 100 as the total number of carbon atoms per one molecule of $R^{21}R^{22}R^{23}R^{24}P^+$.

$R^{21}$ to $R^{24}$ may, respectively, be the same groups or different groups.

Each of $R^{21}$ to $R^{24}$ may be substituted by a functional group inert under the reaction conditions. Such an inert functional group varies depending upon the reaction conditions, but may, for example, be a halogen atom, an ester group, a nitrile group, an acyl group, a carboxy group or an alkoxy group.

Specifically, the quaternary phosphonium ion $R^{21}R^{22}R^{23}R^{24}P^+$ having such $R^{21}$ to $R^{24}$ may, for example, be a tetraethylphosphonium ion, a tetra-n-butylphosphonium ion, a tri-n-octyl ester phosphonium ion, a cetyltriethylphosphonium ion, a cetyltri-n-butylphosphonium ion, a n-butyltriphenylphosphonium ion, a n-amyltriphenylphosphonium ion, a methyltriphenylphosphonium ion, a benzyltriphenylphosphonium ion or a tetraphenylphosphonium ion.

Further, in the above formula (ii), $Y^-$ representing an anion may specifically be e.g. a chlorine ion, a fluorine ion, a bromine ion, an iodine ion, a sulfate ion, a nitrate ion, a phosphate ion, a perchlorate ion, a hydrogen sulfate ion, a hydroxy-ion, an acetate ion, a benzoate ion, a benzene sulfonate ion or a p-toluene sulfonate ion, and a fluorine ion, a chlorine ion or a bromine ion is preferred.

The above quaternary arsonium salt may specifically be a compound represented by the following formula (iii) (hereinafter referred to as compound (iii) as the case requires):

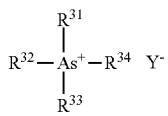

(in the above formula (iii), each of $R^{31}$ to $R^{34}$ which are independent of one another, is a hydrocarbon group, and $Y^-$ is an anion.)

In the above formula (iii), each of $R^{31}$ to $R^{34}$ representing a hydrocarbon group is more specifically a group having the following characteristics.

Each of $R^{31}$ to $R^{34}$ may, for example, be an alkyl group, a cycloalkyl group, an alkenyl group, a cycloalkenyl group or an aryl group, and an alkyl group or an aryl group is preferred.

The number of carbon atoms in $R^{31}$ to $R^{34}$ is preferably from 4 to 100 as the total number of carbon atoms per one molecule of $R^{31}R^{32}R^{33}R^{34}As^+$.

$R^{31}$ to $R^{34}$ may, respectively, be the same groups or different groups.

Each of $R^{31}$ to $R^{34}$ may be substituted by a functional group inert under the reaction conditions. Such an inert functional group varies depending upon the reaction conditions, but may, for example, be a halogen atom, an ester group, a nitrile group, an acyl group, a carboxy group or an alkoxy group.

Further, in the above formula (iii), $Y^-$ representing an anion may be various anions, a halogen ion is preferred, and a fluorine ion, a chlorine ion or a bromine ion is more preferred. The above compound (iii) comprising a quaternary arsonium ion having such $R^{31}$ to $R^{34}$ and $Y^-$, may specifically be triphenylmethylarsonium fluoride, tetraphenylarsonium fluoride, triphenylmethylarsonium chloride, tetraphenylarsonium chloride, tetraphenylarsonium bromide, a polymer derivative thereof, etc.

The above sulfonium salt may, for example, be a compound represented by the following formula (iv) (hereinafter referred to as compound (iv) as the case requires):

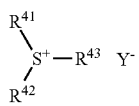

(in the above formula (iv), each of $R^{41}$ to $R^{43}$ which are independent of one another, is a hydrocarbon group, and $Y^-$ is an anion.)

In the above formula (iv), each of $R^{41}$ to $R^{43}$ representing a hydrocarbon group is more specifically a group having the following characteristics.

Each of $R^{41}$ to $R^{43}$ may, for example, be an alkyl group, a cycloalkyl group, an alkenyl group, a cycloalkenyl group or an aryl group, and an alkyl group or an aryl group is preferred.

The number of carbon atoms in $R^{41}$ to $R^{43}$ is preferably from 4 to 100 as the total number of carbon atoms per one molecule of $R^{41}R^{42}R^{43}S^+$.

$R^{41}$ to $R^{43}$ may, respectively, be the same groups or different groups.

Each of $R^{41}$ to $R^{43}$ may be substituted by a functional group inert under the reaction conditions. Such an inert functional group varies depending upon the reaction conditions, but may, for example, be a halogen atom, an ester group, a nitrile group, an acyl group, a carboxy group or an alkoxy group.

$R^{41}$ to $R^{43}$ may be linked to one another to form a hetero ring such as a nitrogen-containing hetero ring.

$R^{41}$ to $R^{43}$ may be a part of a polymer compound.

Further, in the above formula (iv), $Y^-$ representing an anion may be various anions, and a halogen ion is preferred.

The above compound (iv) comprising a sulfonium ion having such $R^{41}$ to $R^{43}$ and $Y^-$ may specifically be e.g. di-n-butylmethylsulfonium iodide, tri-n-butylsulfonium tetrafluoroborate, dihexylmethylsulfonium iodide, dicyclohexylmethylsulfonium iodide, dodecylmethylethylsulfonium chloride or tris(diethylamino)sulfonium difluorotrimethyl silicate.

The above crown ether may specifically be e.g. 18-crown-6 or dibenzo-18-crown-6.

In the present invention, the amount of the above phase transfer catalyst to be used for the dehydrofluorination reaction represented by the above reaction formula (2) is preferably an amount of from 0.001 to 5 mass %, more preferably from 0.01 to 1 mass %, based on the mass of the raw material mixture of HCFC-225 isomers.

Specifically, the dehydrofluorination reaction represented by the above reaction formula (2) is carried out by introducing the above described aqueous alkali solution, the phase transfer catalyst and the reaction raw material composition containing, as the main component, the mixture of HCFC-225 isomers, which contains HCFC-225ca and at least one HCFC-225 isomer other than HCFC-225ca, in the above described proportions and carrying out stirring or the like by a usual means so that they are sufficiently brought in contact with one another. Here, the aqueous alkali solution may be introduced to the above reactor in the form of a basic compound and water, as the case requires.

The reaction temperature in the above dehydrofluorination reaction is not particularly limited, but in the process of the present invention, it is preferably from 0 to 80° C. from the viewpoint of the reaction activity and the selectivity for the desired product. Further, the reaction temperature is suitably adjusted depending upon the pressure state in the reaction container during the reaction. For example, in a case where the above dehydrofluorination reaction is carried out under ordinary pressure, it is preferred to carry out the reaction within a range of from 0 to 60° C., and with a view to more selectively dehydrofluorinating HCFC-225ca in the mixture of HCFC-225 isomers, it is preferred to carry out the reaction within a range of from 30 to 60° C. Further, the above dehydrofluorination reaction may be carried out in a pressurized reactor, and in such a case, from the viewpoint of the reaction rate, preferred conditions may be from 98,000 to 200,000 Pa and from 50 to 80° C.

However, in the present invention, from the viewpoint of formation of by-products i.e. compounds formed as by-products by the dehydrofluorination reaction of HCFC-225X contained as the above described mixture, it is most preferred to carry out the reaction within a temperature range of from 0 to 25° C.

As described above, HCFC-225ca in the mixture of HCFC-225 isomers is selectively dehydrofluorinated to form CFO-1214ya. This reaction may be carried out by either a batch system or a continuous flow system, and the reaction time may suitably be adjusted by a usual method in various manners. Further, the material for the reactor to carry out this reaction may be a usual one such as glass, iron, nickel or an alloy containing such an element as the main component.

According to the process of the present invention, after completion of the dehydrofluorination reaction by the above reaction formula (2), the reaction solution is left to stand, whereby an organic phase and an aqueous phase are naturally separated. In the organic phase, 1,1-dichloro-2,3,3,3-tetrafluoropropene (CFO-1214ya) as the reaction product from HCFC-225ca, and one or more HCFC-225 isomers other than HCFC-225ca not subjected to the dehydrofluorination reaction, are contained. Further, as described above, depending upon the reaction conditions, etc., a very small amount of an isomer of CFO-1214ya having a HCFC-225 isomer other than HCFC-225ca slightly dehydrofluorinated, e.g. 1,3-dichloro-1,2,3,3-tetrafluoropropene (CClF$_2$CF=CClF) having HCFC-225cb (1,3-dichloro-1,2,2,3,3-pentafluoropropane, CHClFCF$_2$CClF$_2$) dehydrofluorinated, may sometimes be contained in the above organic phase. The amount of such a CFO-1214ya isomer slightly present in the organic phase is very small and can be regarded as an amount not influential over the conversion reaction to HFO-1234yf using CFO-1214ya, or use as a refrigerant after the conversion. Such a amount may be influenced by the reaction conditions, etc. in the step of synthesizing HFO-1234yf by hydrogen reduction of CFO-1214ya, but is preferably at most 1,000 ppm.

Here, the difference in boiling point between CFO-1214ya and various HCFC-225 isomers other than HCFC-225ca, is about 10° C. which is within a range where separation and purification are possible by a common method such as distillation, and thus, CFO-1214ya in the organic phase can be easily separated and purified by a usual method and can be used for various applications.

Further, if HCFC-225 isomers other than HCFC-225ca or a mixture of such isomers, not subjected to the dehydrofluorination reaction, obtained from the above organic phase, can be isomerized by e.g. a catalytic reaction as mentioned above (U.S. Pat. No. 5,157,171) to obtain a mixture of HCFC-225 isomers containing HCFC-225ca, such a mixture may be used for the process for producing CFO-1214ya according to the present invention although such may depend also on the types of such isomers.

On the other hand, after completion of the dehydrofluorination reaction represented by the above reaction formula (2), the aqueous phase separated from the above organic phase may be taken out, and an alkali is added thereto to bring its concentration to a proper level, whereupon such an aqueous phase can be re-used.

Now, the process for producing HFO-1234yf of the present invention will be described to produce 2,3,3,3-tetrafluoropropene (CF$_3$CF=CH$_2$, HFO-1234yf) using, as a starting material, 1,1-dichloro-2,3,3,3-tetrafluoropropene (CF$_3$CF=CCl$_2$, CFO-1214ya) obtained by the above described process of the present invention.

To produce HFO-1234yf by using CFO-1214ya obtained as described above, hydrogen is reacted to CFO-1214ya in the presence of a catalyst, as shown by the following reaction formula (3).

[Reaction for forming HFO-1234yf]

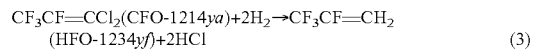

$$CF_3CF{=}CCl_2(CFO\text{-}1214ya)+2H_2 \rightarrow CF_3CF{=}CH_2 \\ (HFO\text{-}1234yf)+2HCl \quad (3)$$

The amount of hydrogen to be used in the reaction to form HFO-1234yf shown by the above reaction formula (3) is specifically usually from 0.5 to 10 mol, preferably from 0.5 to 5 mol, more preferably from 0.5 to 3 mol, per 1 mol of CFO-1214ya. If the amount of hydrogen is at least 0.5 mol per 1 mol of CFO-1214ya, the yield will be high, and deterioration of the catalyst is less likely to occur. Further, when it is at most 3 mol, a side reaction such as reduction or hydrogenation reaction of the desired product is less likely to take place, whereby the yield will be higher.

Further, the catalyst to be used for the reaction for forming HFO-1234yf represented by the above reaction formula (3) may be a catalyst having palladium supported on a carrier or a catalyst having supported on a carrier a metal mixture containing palladium as the main component and having added thereto at least one member selected from Group 10 elements other than palladium, Group 8 elements, Group 9 elements and gold. The above Group 10 elements other than palladium, Group 8 elements and Group 9 elements may be iron, cobalt, nickel, ruthenium, rhodium, iridium, osmium and platinum. Further, the amount of metal other than palladium to be added to the palladium is preferably from 0.01 to 50 parts by weight per 100 parts by weight of palladium. Here, a composite catalyst having another metal added to palladium is effective in that the durability of the catalyst becomes higher than one made solely of palladium.

As the carrier to support the above palladium or metal mixture containing palladium as the main component, activated carbon or a metal oxide such as alumina, zirconia or silica may be used. Among them, activated carbon is preferably employed from the viewpoint of the activities, durability and reaction selectivity. As such activated carbon, one prepared from a raw material such as wood, charcoal, fruit core, coconut shell, peat, lignite or coal may be used, but one obtained from a plant material other than a mineral material is preferred, and particularly, coconut shell activated carbon is most preferred. As the shape of the carrier, formed coal having a length of from about 2 to 5 mm or crushed coal or particulate coal of from about 4 to 50 mesh may be employed, but crushed coal of from 4 to 20 mesh or formed coal is preferred.

The reaction to form HFO-1234yf represented by the above reaction formula (3) is preferably carried out by a gas phase reduction method wherein heated gaseous CFO-1214ya and hydrogen are brought in contact with the catalyst by passing them through a reactor packed with the catalyst at a temperature of from 130 to 250° C., preferably from 150 to 200° C. The reaction usually proceeds sufficiently under ordinary pressure or natural pressure. The contact time with the catalyst may be set to be within a range of usually from 4 to 60 seconds, preferably from 8 to 40 seconds. Further, in order to prevent an excess increase of the temperature, the reaction may be carried out by diluting the reaction atmosphere with an inert gas such as nitrogen.

The amount of the inert gas to be introduced is specifically usually at least 0.1 mol, preferably at least 0.5 mol, per 1 mol of CFO-1214ya. When the amount of the inert gas is at least 0.5 mol per 1 mol of CFO-1214ya, it is possible to suppress heat generation and to suppress formation of by-products, thereby to increase the yield, and at the same time, it is possible to suppress deterioration of the catalyst. The upper limit is not particularly limited, but from the viewpoint of the recovery rate, the amount of the inert gas to be introduced is preferably at most 10 mol, particularly preferably at most 4 mol.

The material for the reactor to be used for the above reaction to form HFO-1234yf may be a usual one, and for example, glass, iron, nickel or an alloy containing such a metal as the main component may be mentioned.

Recovery of 2,3,3,3-tetrafluoropropene ($CF_3CF=CH_2$, HFO-1234yf) as the reaction product and separation of non-reacted materials may be carried out by a usual method, and for example, a common method such as distillation may be employed.

EXAMPLES

Now, the present invention will be described in detail with reference to Examples, but it should be understood that the present invention is by no means restricted by these Examples.

Example 1

Production Example 1 for CFO-1214ya

As a mixture of dichloropentafluoropropane (HCFC-225) isomers, ASAHIKLIN AK-225 (tradename, manufactured by Asahi Glass Company, Limited, mixture of HCFC-225 isomers comprising HCFC-225ca (1,1-dichloro-2,2,3,3,3-pentafluoropropane, $CHCl_2CF_2CF_3$: 48 mol %) and HCFC-225cb (1,3-dichloro-1,2,2,3,3-pentafluoropropane ($CHClFCF_2CClF_2$: 52 mol %)) was used as the reaction raw material, and 1,1-dichloro-2,3,3,3-tetrafluoropropene ($CF_3CF=CCl_2$, CFO-1214ya) was produced by the following process.

Into a glass reactor having an internal capacity of 1 L and provided with a Dimroth condenser cooled to 0° C., 3 g of tetrabutylammonium bromide (TBAB) as a phase transfer catalyst, 83 g of potassium hydroxide (1.485 mol), 180 g of water and 609 g (3.0 mol) of ASAHIKLIN AK225 were charged, and then, the temperature was gradually raised with stirring, and a reaction was carried out at 45° C. for 1 hour. After completion of the reaction, a part of an organic phase of the reaction crude liquid was recovered, and the composition was analyzed by gas chromatography (GC). The analytical results are shown in Table 1.

Further, after the GC analysis, the reaction crude liquid separated into two phases of an organic phase and an aqueous phase was subjected to liquid separation, and the organic phase was charged into a distillation tower having a capacity of 1 L and an ability of a theoretical plate number of 10 plates, followed by distillation. As a result of the distillation, it was possible to recover 262 g (1.43 mol) of CFO-1214ya (boiling point: 45° C.) having a purity of 99.5%.

TABLE 1

| | Molar composition (%) | |
|---|---|---|
| | Composition of raw material liquid | Composition of reaction crude liquid |
| HCFC-225ca | 48 | 0 |
| HCFC-225cb | 52 | 52 |
| CFO-1214ya | 0 | 48 |

Examples 1-1 to 1-4

Production Examples 1-1 to 1-4 for CFO-1214ya

Using the same reaction apparatus as used in Example 1, 3 g of tetrabutylammonium bromide (TBAB) as a phase transfer catalyst, 83 g of potassium hydroxide (1.485 mol), 124 g of water and 609 g (3.0 mol) of ASAHIKLIN AK-225 were charged, and then a reaction was carried out for 1 hour at a temperature shown in Table 2 with stirring. After completion of the reaction, a part of the organic phase of the reaction crude liquid was recovered, and the composition was analyzed by gas chromatography (GC). The analytical results are shown in Table 2.

TABLE 2

| | Ex. | | | | | | | |
|---|---|---|---|---|---|---|---|---|
| | 1-1 | | 1-2 | | 1-3 | | 1-4 | |
| | Temperature (° C.) | | | | | | | |
| | 5 | | 15 | | 25 | | 30 | |
| | Molar composition (%) | | Molar composition (%) | | Molar composition (%) | | Molar composition (%) | |
| | Composition of raw material liquid | Composition of reaction crude liquid | Composition of raw material liquid | Composition of reaction crude liquid | Composition of raw material liquid | Composition of reaction crude liquid | Composition of raw material liquid | Composition of reaction crude liquid |
| HCFC-225ca | 48 | 10 | 48 | 0 | 48 | 0 | 48 | 0 |
| HCFC-225cb | 52 | 52 | 52 | 52 | 52 | 52 | 52 | 51.7 |
| HFO-1214ya | 0 | 38 | 0 | 48 | 0 | 48 | 0 | 48 |
| HFO-1214yb | 0 | 0 | 0 | 0 | 0 | 0 | 0 | 0.3 |

Example 2

Production Example for HFO-1234yf

Activated carbon (tradename: Shirasagi C2X, manufactured by Takeda Pharmaceutical Company Limited) catalyst having 2 mass % of palladium supported thereon was packed in a reaction tube made of Inconel (registered trademark) 600 having an inner diameter of 2.54 cm and a length of 100 cm, and immersed in a salt bath. Using 1,1-dichloro-2,3,3,3-tetrafluoropropene ($CF_3CF=CCl_2$, CFO-1214ya) obtained in the above Example 1, a reduction reaction was carried out under the reaction conditions shown in the upper rows in Table 3 to produce 2,3,3,3-tetrafluoropropene ($CF_3CF=CH_2$, HFO-1234yf).

Confirmation of the reaction products was carried out by analyzing the outlet gas from the reactor by gas chromatography and calculating the molar composition of the crude gas. The results are shown in the lower rows in Table 3.

TABLE 3

| | | |
|---|---|---|
| Reaction conditions | Reaction temperature | 200° C. |
| | Raw material supply ratio ($CFO-1214ya/H_2/N_2$) | 1/2/2 (molar ratio) |
| | Contact time | 53 Seconds |
| Crude gas composition | $CF_3CF=CCl_2$ (CFO-1214ya) | 0% |
| | $CF_3CF=CH_2$ (HFO-1234yf) | 72% |
| | Others | 28% |

Examples 2-1 and 2-2

Production Examples 2-1 and 2-2 for HFO-1234yf

Activated carbon (tradename: Shirasagi C2X, manufactured by Takeda Pharmaceutical Company Limited) catalyst having 1.8 mass % of palladium and 0.2 mass % of gold supported thereon, was packed in a reaction tube made of Inconel (registered trademark) 600 having an inner diameter of 2.54 cm and a length of 100 cm, and immersed in a salt bath. Using 1,1-dichloro-2,3,3,3-tetrafluoropropene ($CF_3CF=CCl_2$, CFO-1214ya) obtained in the above Example 1, a reduction reaction was carried out under the reaction conditions shown in the upper rows in Table 4 to produce 2,3,3,3-tetrafluoropropene ($CF_3CF=CH_2$, HFO-1234yf). Confirmation of the reaction products was carried out by analyzing the outlet gas from the reactor by gas chromatography and calculating the molar composition of the crude gas. The results are shown in the lower rows in Table 4.

TABLE 4

| | Ex. | 2-1 | 2-2 |
|---|---|---|---|
| Reaction conditions | Reaction temperature | 180° C. | 180° C. |
| | Raw material supply ratio ($CFO-1214ya/H_2/N_2$) | 1/2/3.4 (molar ratio) | 1/2/0.1 (molar ratio) |
| | Contact time | 60 Seconds | 60 Seconds |
| Crude gas composition | $CF_3CF=CCl_2$ (CFO-1214ya) | 30% | 18% |
| | $CF_3CF=CH_2$ (HFO-1234yf) | 42% | 36% |
| | Others | 28% | 46% |

Examples 2-3 and 2-4

Production Examples 2-3 and 2-4 for HFO-1234yf

Activated carbon (tradename: Shirasagi C2X, manufactured by Takeda Pharmaceutical Company Limited) catalyst having 0.5 mass % of palladium supported thereon, was packed into a reaction tube made of Inconel (registered trademark) 600 having an inner diameter of 2.54 cm and a length of 100 cm, and immersed in a salt bath. Using 1,1-dichloro-2,3,3,3-tetrafluoropropene ($CF_3CF=CCl_2$, CFO-1214ya) obtained in the above Example 1, a reduction reaction was carried out under the reaction conditions shown in the upper rows in Table 5 to produce 2,3,3,3-tetrafluoropropene ($CF_3CF=CH_2$, HFO-1234yf).

Confirmation of the reaction products was carried out by analyzing the outlet gas from the reactor by gas chromatography and calculating the molar composition of the crude gas. The results are shown in the lower rows in Table 5.

TABLE 5

| | Ex. | 2-3 | 2-4 |
|---|---|---|---|
| Reaction conditions | Reaction temperature | 180° C. | 180° C. |
| | Raw material supply ratio ($CFO-1214ya/H_2/N_2$) | 1/2/3 (molar ratio) | 1/3/3 (molar ratio) |
| | Contact time | 30 Seconds | 30 Seconds |
| Crude gas composition | $CF_3CF=CCl_2$ (CFO-1214ya) | 1% | 0% |
| | $CF_3CF=CH_2$ (HFO-1234yf) | 70% | 20% |
| | Others | 29% | 80% |

Example 3

Production Example for CFO-1214ya

Preparation of Partially Fluorinated Aluminum Chloride

Firstly, partially fluorinated aluminum chloride as a Lewis acid catalyst was prepared as follows.

That is, a Dimroth condenser having circulated a cooling medium cooled to −20° C., was set on a three-necked flask (internal capacity: 500 mL), and 50 g (0.375 mol) of aluminum trichloride ($AlCl_3$) was charged thereto and cooled to 0° C., whereupon 175 mL (262.5 g; 1.9 mol) of trichlorofluoromethane ($CFCl_3$) was slowly dropwise added with stirring.

While generating a low boiling point gas, isomerization of trichlorofluoromethane proceeded. Along with the progress of this isomerization, a halogen exchange reaction proceeded between aluminum trichloride ($AlCl_3$) as the catalyst and chlorofluoromethane as the substrate to form fluorine-substituted aluminum halide. The reaction was continued for one hour, and then, the volatile component was removed, and the catalyst was dried. Thus, partially fluorinated aluminum chloride was obtained.

Preparation of Mixture of HCFC-225 Isomers

Then, into a glass reactor (internal capacity: 1 L) provided with a Dimroth condenser cooled to 0° C., 10 g of the partially fluorinated aluminum chloride obtained by the above reaction was put as a catalyst, and 609 g (3.0 mol) of ASAHIKLIN AK225 (tradename, manufactured by Asahi Glass Company, Limited, a mixture of HCFC-225 isomers comprising HCFC-225ca (48 mol %) and HCFC-225cb (52 mol %)) was added thereto as a mixture of dichloropentafluoropropane (HCFC-225) isomers. The composition of the raw material liquid (the molar ratio of isomers) is shown in Table 6.

After adding such a raw material liquid, the temperature in the reactor was heated to 50° C., and a reaction was carried out for 20 hours with stirring. After the reaction, the liquid was filtrated to remove the catalyst and to recover 600 g of the reaction product liquid. Then, with respect to the obtained reaction product liquid, an analysis by gas chromatography was carried out to obtain the composition of the reaction products. The results are shown in Table 6. Here, HCFC-225aa in the Table represents 2,2-dichloro-1,1,3,3,3-pentafluoropropane ($CHF_2CCl_2CF_3$).

TABLE 6

|  | Molar composition (%) | |
| --- | --- | --- |
|  | Composition of raw material liquid | Composition of reaction product liquid |
| HCFC-225ca | 48 | 75 |
| HCFC-225cb | 52 | 1 |
| HCFC-225aa | 0 | 19 |
| Other HCFC-225 isomers | 0 | 5 |

Production of CFO-1214ya

Using the mixture recovered as the reaction products, as the reaction raw material, 1,1-dichloro-2,3,3,3-tetrafluoropropene ($CF_3CF=CCl_2$, CFO-1214ya) was produced by the following process.

Into a glass reactor having an internal capacity of 1 L and provided with a Dimroth condenser cooled to 0° C., 3 g of tetrabutylammonium bromide (TBAB) as a phase transfer catalyst, 129 g of potassium hydroxide (2.30 mol), 220 g of water, and 600 g (2.96 mol) of the above recovered composition were charged, and then, the temperature was gradually raised with stirring, and a reaction was carried out at 45° C. for 1 hour. After completion of the reaction, a part of the organic phase of the reaction crude liquid was recovered, and the composition was analyzed by gas chromatography (GC). The analytical results are shown in Table 7. Further, after the GC analysis, the reaction crude liquid separated into two phases of an organic phase and an aqueous phase, was subjected to liquid separation, and the organic phase was charged into a distillation tower having a capacity of 1 L and an ability of theoretical plate number of 10 plates, followed by distillation. As a result of the distillation, it was possible to recover 384 g (2.10 mol) of CFO-1214ya (boiling point: 45° C.) having a purity of 99.5%.

TABLE 7

|  | Molar composition (%) | |
| --- | --- | --- |
|  | Composition of raw material liquid | Composition of reaction product liquid |
| HCFC-225ca | 75 | 0 |
| HCFC-225cb | 1 | 1 |
| HCFC-225aa | 19 | 19 |
| Other HCFC-225 isomers | 5 | 5 |
| CFO-1214ya | 0 | 75 |

Industrial Applicability

According to the process of the present invention, it is possible to produce 1,1-dichloro-2,3,3,3-tetrafluoropropene (CFO-1214ya) which is useful as a synthetic raw material for 2,3,3,3-tetrafluoropropene (HFO-1234yf) useful as a new refrigerant, simply and economically without requiring purification of the raw material component obtained as a mixture of isomers i.e. 1,1-dichloro-2,2,3,3,3-pentafluoropropane (HCFC-225ca).

Here, 2,3,3,3-tetrafluoropropene (HFO-1234yf) is a compound which has been expected in recent years as a new refrigerant which may be substituted for 1,1,1,2-tetrafluoroethane (HFC-134a) being a greenhouse gas.

The entire disclosure of Japanese Patent Application No. 2008-331321 filed on Dec. 25, 2008 including specification, claims and summary is incorporated herein by reference in its entirety.

What is claimed is:

1. A process for producing 1,1-dichloro-2,3,3,3-tetrafluoropropene, comprising contacting a mixture of dichloropentafluoropropane isomers which comprises 1,1-dichloro-2,2,3,3,3-pentafluoropropane with an aqueous alkali solution in the presence of a phase transfer catalyst, and thereby selectively dehydrofluorinating only the 1,1-dichloro-2,2,3,3,3-pentafluoropropane in the mixture.

2. The process for producing 1,1-dichloro-2,3,3,3-tetrafluoropropene according to claim 1, wherein the mixture of dichloropentafluoropropane isomers comprises, in addition to the 1,1-dichloro-2,2,3,3,3-pentafluoropropane, at least one isomer selected from 1,3-dichloro-1,2,2,3,3-pentafluoropropane, 2,2-dichloro-1,1,3,3,3-pentafluoropropane, 1,2-dichloro-1,2,3,3,3-pentafluoropropane and 2,3-dichloro-1,1,2,3,3-pentafluoropropane.

3. The process for producing 1,1-dichloro-2,3,3,3-tetrafluoropropene according to claim 1, wherein the content of the 1,1-dichloro-2,2,3,3,3-pentafluoropropane in the mixture of dichloropentafluoropropane isomers is at most 99.5 mol %.

4. The process for producing 1,1-dichloro-2,3,3,3-tetrafluoropropene according to claim 1, wherein the concentration of the aqueous alkali solution is from 0.5 mass % to 40 mass %.

5. The process for producing 1,1-dichloro-2,3,3,3-tetrafluoropropene according to claim 1, wherein the temperature at which the mixture of dichloropentafluoropropane isomers is brought into contact with the aqueous alkali solution in the presence of a phase transfer catalyst is from 0 to 80° C.

6. The process for producing 1,1-dichloro-2,3,3,3-tetrafluoropropene according to claim 1, wherein the temperature at which the mixture of dichloropentafluoropropane isomers is brought into contact with the aqueous alkali solution in the presence of a phase transfer catalyst is from 0 to 25° C.

7. A process for producing 2,3,3,3-tetrafluoropropene, which comprises reacting the 1,1-dichloro-2,3,3,3-tetrafluoropropene obtained by the process as defined in claim 1, with hydrogen in the presence of a catalyst.

8. The process for producing 2,3,3,3-tetrafluoropropene according to claim 7, wherein the amount of the hydrogen which is used for the reaction for forming the 2,3,3,3-tetrafluoropropene, is less than 3 mol to 1 mol of the 1,1-dichloro-2,3,3,3-tetrafluoropropene.

9. The process for producing 2,3,3,3-tetrafluoropropene according to claim 7, wherein the reaction for forming the 2,3,3,3-tetrafluoropropene is carried out in the presence of an inert gas.

10. The process for producing 2,3,3,3-tetrafluoropropene according to claim 9, wherein the reaction for forming the 2,3,3,3-tetrafluoropropene is carried out in the presence of an inert gas in an amount of at least 0.5 time by mol to the 1,1-dichloro-2,3,3,3-tetrafluoropropene.

11. The method of claim 1, wherein said aqueous alkali solution comprises at least one alkali selected from the group consisting of sodium hydroxide and potassium hydroxide.

12. The method of claim 1, wherein an amount of said aqueous alkali solution is 0.5 to 1.5 mol equivalents to an amount of 1,1-dichloro-2,2,3,3,3-pentafluoropropane.

13. The method of claim 1, wherein said phase transfer catalyst is at least one catalyst selected from the group consisting of a quaternary ammonium salt, a quaternary phosphonium salt substituted by a hydrocarbon group and a crown ether.

14. The method of claim 1, wherein said phase transfer catalyst is in an amount of 0.001 to 5 mass % to a mass of said 1,1-dichloro-2,2,3,3,3-pentafluoropropane.

15. The method of claim 1, wherein said phase transfer catalyst is in an amount of 0.01 to 1 mass % to a mass of said 1,1-dichloro-2,2,3,3,3-pentafluoropropane.

16. The process for producing 1,1-dichloro-2,3,3,3-tetrafluoropropene according to claim 1, wherein the content of the 1,1-dichloro-2,2,3,3,3-pentafluoropropane in the mixture of dichloropentafluoropropane isomers is at least 10 mol %.

17. The process for producing 1,1-dichloro-2,3,3,3-tetrafluoropropene according to claim 1, wherein the content of the 1,1-dichloro-2,2,3,3,3-pentafluoropropane in the mixture of dichloropentafluoropropane isomers is at least 48 mol %.

18. The process for producing 1,1-dichloro-2,3,3,3-tetrafluoropropene according to claim 1, wherein said mixture of dichloropentafluoropropane isomers is brought into contact with the aqueous alkali solution in the presence of a phase transfer catalyst at at pressure of 98,000-200,000 Pa and a temperature of 50-80° C.

* * * * *